(12) United States Patent
Maekawa

(10) Patent No.: US 8,759,354 B2
(45) Date of Patent: Jun. 24, 2014

(54) PHARMACEUTICAL COMPOSITION COMPRISING PYRAZINE DERIVATIVE, AND METHOD OF USING PYRAZINE DERIVATIVE IN COMBINATION

(75) Inventor: Masako Maekawa, Toyama (JP)

(73) Assignee: Toyama Chemical Co., Ltd., Tokyo (JP)

( * ) Notice: Subject to any disclaimer, the term of this patent is extended or adjusted under 35 U.S.C. 154(b) by 742 days.

(21) Appl. No.: 12/527,260

(22) PCT Filed: Feb. 14, 2008

(86) PCT No.: PCT/JP2008/052425
§ 371 (c)(1),
(2), (4) Date: Aug. 14, 2009

(87) PCT Pub. No.: WO2008/099874
PCT Pub. Date: Aug. 21, 2008

(65) Prior Publication Data
US 2010/0087447 A1    Apr. 8, 2010

(30) Foreign Application Priority Data

Feb. 16, 2007  (JP) ................................. 2007-035975

(51) Int. Cl.
  *A61K 31/4965*  (2006.01)
  *A61K 31/35*    (2006.01)
  *A61K 31/22*    (2006.01)
  *A61K 31/225*   (2006.01)

(52) U.S. Cl.
USPC ....... 514/255.06; 514/459; 514/546; 514/547

(58) Field of Classification Search
USPC .............................. 514/255.06, 459, 546, 547
See application file for complete search history.

(56) References Cited

U.S. PATENT DOCUMENTS

| 6,787,544 B2 * | 9/2004 | Furuta et al. ................... 514/241 |
| 2002/0013316 A1 | 1/2002 | Furuta et al. |
| 2004/0235761 A1 | 11/2004 | Furuta et al. |

FOREIGN PATENT DOCUMENTS

| EP | 1 112 743 A1 | 7/2001 |
| JP | 1 197437 | 8/1989 |
| RU | 2 224 520 C2 | 2/2004 |
| WO | 00 10569 | 3/2000 |
| WO | 03 015798 | 2/2003 |

OTHER PUBLICATIONS

Yamashita "New anti-influenza compound: second-generation anti-influenza compound CS-8958," Kagaku Ryoho no Ryoiki, 2005, vol. 21, No. 12, pp. 1767-1773. CAPLUS Abstract, DN 144:403607.*
Singaporean Written Opinion and Search Report issued on Jan. 5, 2011 in corresponding Singaporean Application No. 200905274-7.
Y. Furuta et al., "In Vitro and In Vivo Activities of Anti-Influenza Virus Compound T-705", Antimicrobial Agents and Chemotherapy, Apr. 2002, vol. 46, No. 4, pp. 977-981.
Robert W. Sidwell et al., "Efficacy of Orally Administered T-705 on Lethal Avian Influenza A (H5N1) Virus Infections in Mice", Antimicrobial Agents and Chemotherapy, Mar. 2007, vol. 51, No. 3, pp. 845-851.
Elena A. Govorkova et al., "Neuraminidase Inhibitor-Rimantadine Combinations Exert Additive and Synergistic Anti-Influenza Virus Effects in MDCK Cells", Antimicrobial Agents and Chemotherapy, Dec. 2004, vol. 48, No. 12, pp. 4855-4863 (Database CAplus on STN Abstract previously filed on Aug. 14, 2009, submitting complete reference).
K. Takahashi et al., "In Vitro and In Vivo Activities of T-705 and Oseltamivir Against Influenza Virus", Antivir. Chem. Chemother., Sep. 2003, vol. 14, No. 5, pp. 235-241 (Database CAplus on STN Abstract previously filed on Aug. 14, 2009, submitting English Abstract only).
Natalia A. Ilyushina et al., "Combination Chemotherapy, A Potential Strategy for Reducing the Emergence of Drug-Resistant Influenza A Variants", Antiviral Research, Jul. 2006, vol. 70, pp. 121-131.
Extended European Search Report issued Apr. 19, 2011, in Patent Application No. 08711267.8.
Yousuke Furuta, et al., "Mechanism of Action of T-705 against Influenza Virus", Antimicrobial Agents and Chemotherapy, vol. 49 No. 3, XP 2631742, Mar. 2005 pp. 981-986.
Govorkova, E. A. et al., Neuraminidase inhibitor-rimantadine combinations exert additive and synergistic anti-influenza virus effects in MDCK Cells, Antimicrobial Agents and Chemotheraphy, vol. 48, No. 12, p. 4855-4863, (2004).
Shigeta, S., "Recent progress in anti-influenza chemotheraphy", Drugs in R & D, vol. 2, No. 3, p. 153-164, (1999).

(Continued)

*Primary Examiner* — Shengjun Wang
(74) *Attorney, Agent, or Firm* — Oblon, Spivak, McClelland, Maier & Neustadt, L.L.P.

(57) ABSTRACT

Disclosed is a pharmaceutical composition comprising a pyrazine derivative represented by the general formula:

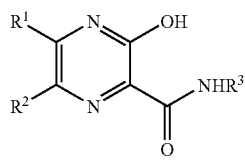

[1]

[wherein $R^1$ and $R^2$ independently represent a hydrogen atom or a halogen atom; and $R^3$ represents a hydrogen atom or an amino-protecting group] or a salt thereof and at least one neuraminidase inhibitor. The pharmaceutical composition is useful for a treatment including the treatment or prevention of influenza. Also disclosed is a method of using these components in combination. The method is useful for a treatment including the treatment or prevention of influenza.

12 Claims, No Drawings

(56) References Cited

OTHER PUBLICATIONS

Madren, L. K. et al., "In vitro inhibitory effects of combinations of anti-influenza agents", Antiviral Chemistry & Chemotheraphy, vol. 6, No. 2, p. 109-113, (1995).

Takahashi, K. et al., "In vitro and in vivo activities of T-705 and oseltamivir against influenza virus", Antiviral Chemistry & Chemotheraphy, vol. 14, No. 5, p. 235-241, (2003).

Kaji, M. et al., "Neuraminidase inhibitor, anti-influenzal agent Mechanism of action, and how to use clinically", Japanese Journal of Clinical Medicine, vol. 61, No. 11, p. 1975-1979, (2003), (with English abstract).

Office Action issued Jul. 13, 2011, in Russian Patent Application No. 2009134516/15 (with English-language translation).

M. Von Itzstein, et al., "Sialic Acids and Sialic Acid-Recognising Proteins: Drug Discovery Targets and Potential Glycopharmaceuticals", Current Medicinal Chemistry, vol. 4, No. 3, 1997, pp. 185-210.

Theodora W. Greene, et al., "Protective Groups in Organic Synthesis", $3^{rd}$ Edition, 1999, p. 1 and 494-653.

U.S. Appl. No. 13/877,037, filed May 9, 2013, Takakura, et al.

U.S. Appl. No. 13/876,998, filed Mar. 29, 2013, Takakura, et al.

\* cited by examiner

PHARMACEUTICAL COMPOSITION COMPRISING PYRAZINE DERIVATIVE, AND METHOD OF USING PYRAZINE DERIVATIVE IN COMBINATION

CROSS-REFERENCE TO RELATED APPLICATIONS

This application is a 371 of PCT/JP08/052,425 filed Feb. 14, 2008 and claims the benefit of JP 2007-035975 filed Feb. 16, 2007.

TECHNICAL FIELD

The present invention relates to a pharmaceutical composition comprising a pyrazine derivative or a salt thereof and one or more neuraminidase inhibitor(s), which is useful in the treatment (e.g., therapy or prevention) of viral diseases. Moreover, the present invention relates to a method of using a pyrazine derivative or a salt thereof and neuraminidase inhibitor(s) in combination for treatment (e.g., therapy or prevention) of influenza.

BACKGROUND ART

Influenza virus infection (hereinafter, referred to as influenza) caused by influenza virus is frequently a fatal disease. In recent years, viruses such as avian influenza have occurred, which exhibit strong pathogenicity to humans. Avian influenza threatens to be pandemic.

However, drugs applicable to influenza are much fewer than antimicrobial agents or the like. For example, amantadine and oseltamivir currently used have problems such as resistance to them.

A method of using anti-influenza virus agents in combination has been discussed for the purpose of reducing drug resistance of influenza virus, enhancing therapeutic effects, and/or reducing side effects, etc. However, the drugs used in combination are limited in number and do not always produce satisfactory effects.

For example, neuraminidase inhibitors are known as drugs that exhibit effects on influenza virus. Neuraminidase, which is a spike glycoprotein found on the surface of influenza virus, is required for influenza virus infecting cells of the throat or bronchus and proliferating to spread to their neighboring cells. The inhibition of neuraminidase may suppress the spread of such influenza virus to the neighboring cells. For example, a neuraminidase inhibitor oseltamivir is converted to its active form GS-4071 in vivo, which exhibits antiviral effects such that it inhibits neuraminidase on influenza virus (NON-PATENT DOCUMENT 1). Oseltamivir and zanamivir are commercially available as neuraminidase inhibitors. Such drugs have still been developed and studied.

On the other hand, a pyrazine derivative having antiviral activities is known (PATENT DOCUMENT 1). This pyrazine derivative is known to exhibit antiviral effects upon intracellular ribosylphosphorylation such that it inhibits virus RNA polymerase (PATENT DOCUMENT 2).

However, neither a pharmaceutical composition comprising a neuraminidase inhibitor and a pyrazine derivative nor a method of using a neuraminidase inhibitor and a pyrazine derivative in combination has been known so far.
PATENT DOCUMENT 1: Pamphlet of WO00/10569
PATENT DOCUMENT 2: Pamphlet of WO03/015798
NON-PATENT DOCUMENT 1: Japanese Journal of Clinical Medicine, 2003, vol. 61, p. 1975-1979

DISCLOSURE OF THE INVENTION

Problems to be Solved by the Invention

There has been a demand for a pharmaceutical composition which has strong anti-influenza virus activities with few side effects and is useful for the treatment (e.g., therapy or prevention) of influenza and for a method of treatment of influenza.

Means for Solving the Problems

Under such circumstances, the present inventor has conducted diligent studies and consequently completed the present invention by finding that a pharmaceutical composition comprising a pyrazine derivative represented by the following general formula [1] a salt thereof and one or more neuraminidase inhibitor(s):

[Formula 1]

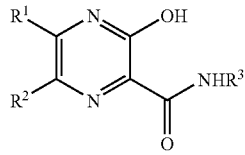

[1]

wherein $R^1$ and $R^2$ are the same or different and each represents a hydrogen atom or a halogen atom; and $R^3$ represents a hydrogen atom or an amino-protecting group, has strong anti-influenza virus activities and is useful for the treatment of influenza, and that a method of using these compounds in combination is useful as a method of treatment of influenza.

Advantages of the Invention

A pharmaceutical composition comprising a pyrazine derivative or a salt thereof and one or more neuraminidase inhibitor(s) has synergistic strong anti-influenza virus activities and is useful for the treatment (e.g., therapy or prevention) of influenza. A method of using these compounds in combination is useful as a method of treatment (e.g., therapy or prevention) of influenza.

BEST MODE FOR CARRYING OUT THE INVENTION

Hereinafter, the present invention will be described in detail.

In the present specification, unless otherwise specified, a halogen atom means fluorine, chlorine, bromine, and iodine atoms; an acyl group means, for example, a formyl group, a linear or branched $C_{2-12}$ alkanoyl group (e.g., acetyl, propionyl, butyryl, isovaleryl, and pivaloyl), an ar-$C_{1-6}$ alkylcarbonyl group (e.g., benzylcarbonyl), a cyclic hydrocarbon carbonyl group (e.g., benzoyl and naphthoyl), a heterocyclic carbonyl group (e.g., nicotinoyl, thenoyl, pyrrolidinocarbonyl, and furoyl), a succinyl group, a glutaryl group, a maleoyl group, a phthaloyl group, and a linear or branched α-aminoalkanoyl group (which may be N-terminally protected) derived from amino acids (examples of the amino acids include glycine, alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, proline, and hydroxyproline); an alkyloxycarbonyl group means, for example, a linear or branched $C_{1-12}$ alkyloxycarbonyl group such as methoxycarbonyl, ethoxycarbonyl, 1,1-dimethylpropoxycarbonyl, isopropoxycarbonyl, 2-ethylhexyloxycarbonyl, tert-butoxycarbonyl, and tert-pentyloxycarbonyl; an aralkyloxycarbonyl group means, for example, an ar-$C_{1-6}$ alkyloxycarbonyl group such as benzyloxycarbonyl and phenethyloxycarbonyl groups; an aryloxycarbonyl group means, for example, a phenyloxycarbonyl group; an aralkyl group means, for example, an ar-$C_{1-6}$ alkyl group such as benzyl, diphenylmethyl, trityl, phenethyl, and naphthylmethyl; an alkoxyalkyl group means, for example, a $C_{1-6}$ alkyloxy-$C_{1-6}$ alkyl group such as methoxymethyl and 1-ethoxyethyl; an aralkyloxyalkyl group means, for example, an ar-$C_{1-6}$ alkyloxy-$C_{1-6}$ alkyl group such as benzyloxymethyl and phenethyloxymethyl;

an arylthio group means, for example, a phenylthio group; an alkylsulfonyl group means, for example, a $C_{1-6}$ alkylsulfonyl group such as methylsulfonyl, ethylsulfonyl, and propylsulfonyl; an arylsulfonyl group means, for example, benzenesulfonyl, toluenesulfonyl, and naphthalenesulfonyl groups; a dialkylaminoalkylidene group means, for example, N,N-dimethylaminomethylene and N,N-diethylaminomethylene groups; an aralkylidene group means, for example, benzylidene and naphthylmethylene groups; a nitrogen-containing heterocyclic alkylidene group means, for example, a 3-hydroxy-4-pyridylmethylene group; a cycloalkylidene group means, for example, cyclopentylidene and cyclohexylidene groups; a diarylphosphoryl group means, for example, a diphenylphosphoryl group; a diaralkylphosphoryl group means, for example, a dibenzylphosphoryl group; an oxygen-containing heterocyclic alkyl group means, for example, a 5-methyl-2-oxo-2H-1,3-dioxol-4-ylmethyl group; and a substituted silyl group means, for example, trimethylsilyl, triethylsilyl, and tributylsilyl groups.

An amino-protecting group encompasses all groups available as usual amino-protecting groups. Examples thereof include groups described in W. Greene et al., Protective Groups in Organic Synthesis, 3rd ed., p. 494-653, 1999, John Wiley & Sons, INC. Specific examples thereof include an acyl group, an alkyloxycarbonyl group, an aralkyloxycarbonyl group, an aryloxycarbonyl group, an aralkyl group, an alkoxyalkyl group, an aralkyloxyalkyl group, an arylthio group, an alkylsulfonyl group, an arylsulfonyl group, a dialkylaminoalkylidene group, an aralkylidene group, a nitrogen-containing heterocyclic alkylidene group, a cycloalkylidene group, a diarylphosphoryl group, a diaralkylphosphoryl group, an oxygen-containing heterocyclic alkyl group, and a substituted silyl group.

Examples of a salt of the compound of the general formula [1] used in the present invention may include usually known salts of hydroxyl groups. Examples thereof may include: salts with alkali metals such as sodium and potassium; salts with alkaline-earth metals such as calcium and magnesium; ammonium salts; and salts with nitrogen-containing organic bases such as trimethylamine, triethylamine, tributylamine, N-methylpiperidine, N-methylmorpholine, diethylamine, dicyclohexylamine, procaine, dibenzylamine, N-benzyl-β-phenethylamine, 1-ephenamine, and N,N'-dibenzylethylenediamine.

Desirable examples of the salt include pharmacologically acceptable salts. A salt with sodium is preferable.

Desirable examples of the compound of the general formula [1] used in the present invention include the following compounds:

compounds represented by the general formula [1] wherein $R^1$ is a hydrogen atom, $R^2$ is a fluorine atom, and $R^3$ is a hydrogen atom.

The compound of the general formula [1] used in the present invention is produced by combining methods known per se in the art and may be produced according to, for example, a production method described in PATENT DOCUMENT 1.

Examples of a neuraminidase inhibitor used in the present invention include compounds themselves or their in-vivo metabolites having inhibitory effects on neuraminidase, such as oseltamivir, zanamivir, peramivir, CS-8958 and FRUNET. Oseltamivir and zanamivir are preferable. Oseltamivir is furthermore desirable.

The administration route of a pharmaceutical composition of the present invention is not particularly limited, and it may be administered intravenously, orally, intramuscularly, hypodermically, by inhalation, by spraying, or through other administration routes. Moreover, the pyrazine derivative represented by the general formula [1] or the salt thereof may be administered with the neuraminidase inhibitor simultaneously or in a particular order.

The pharmaceutical composition of the present invention is useful for the treatment (e.g., therapy or prevention) of influenza.

The pharmaceutical composition of the present invention allows treatment (e.g., therapy or prevention) of more severe influenza. Moreover, the individual drugs used exhibit strong anti-influenza virus effects even when they are administered in decreased amounts. Therefore, their respective side effects can be reduced.

When the pharmaceutical composition of the present invention is used, it may usually be mixed appropriately with pharmaceutical aids used in formulation, such as an excipient, a carrier, and a diluent. These formulations may be administered orally or parenterally in a form such as a tablet, a capsule, a powder, a syrup, a granule, a pill, a suspension, an emulsion, a solution, a powdered preparation, a suppository, eye drops, nasal drops, eardrops, a patch, an ointment, or an injection according to a conventional method. Moreover, an administration method, a dose, and the frequency of administration may be selected appropriately according to the age, body weight, and symptom of a patient. It may usually be administered orally or parenterally (e.g., injection, intravenous drips, and administration to a rectal site) to an adult in one to several divided dose(s) at dose(s) of 0.01 to 1000 mg/kg per day.

EXAMPLES

Next, the present invention will be described with reference to Test Examples. However, the present invention is not intended to be limited to them.

6-Fluoro-3-hydroxy-2-pyrazinecarboxamide (hereinafter, referred to as T-705) was selected as a test compound. GS-4071, which is an in-vivo active form of oseltamivir, and zanamivir were selected as neuraminidase inhibitors. In this context, GS-4071 used in the present tests was obtained by extraction from Tamiflu (commercially available drug), followed by hydrolysis according to a conventional method.

Test Example 1

T-705 was selected as a test compound. GS-4071 was selected as a neuraminidase inhibitor.

(1) Culture of MDCK Cells

Madin-Darby Canine Kidney (hereinafter, referred to as MDCK) cells subcultured at 37° C. under 5% carbon dioxide conditions in an Eagle's MEM medium supplemented with 10% fetal bovine serum in the culture solution were dissociated by an ethylenediaminetetraacetic acid-trypsin method and suspended in the same medium as above. The cell suspension prepared to contain $2 \times 10^4$ cells in 100 μL was in turn inoculated to a 96-well plate. The cells were cultured overnight at 37° C. under 5% carbon dioxide conditions to obtain a monolayer of MDCK cells.

(2) Influenza Virus Infection and Drug Addition

A test medium used was a medium prepared by adding L-1-tosylamido-2-phenylethyl chloromethyl ketone (TPCK)-treated trypsin at a concentration of 3 μg/mL to an Eagle's MEM medium containing 1% bovine serum albumin supplemented with 60 μg/mL kanamycin and four times the usual concentration of vitamins.

The MDCK cells obtained in the paragraph (1) were rinsed with an Eagle's MEM medium after removal of the culture supernatant. Then, to each well, the following agents were added: 100 μL of an Eagle's MEM medium containing bovine serum albumin and vitamins at two times the concentration of the test medium; 50 μL of an influenza virus (PR/8 (H1N1)) solution adjusted to $4.0 \times 10^3$ PFU/mL with an Eagle's MEM medium containing TPCK-treated trypsin at four times the concentration of the test medium; and 50 μL of an Eagle's MEM medium containing T-705 or GS-4071 at four times the target concentration (T-705 target concentration (μg/mL): 0.0156, 0.0313, 0.0625, 0.125, 0.25, 0.5, 1, 2, and 4; and GS-4071 target concentration (μg/mL): 0.00313, 0.00625, 0.0125, 0.025, 0.05, 0.1, 0.2, 0.4, and 0.8) or containing a T-705/GS-4071 (5:1 ratio by weight concentration) mixture at the four times the target concentration.

After drug addition, the cells were cultured at 35° C. for 2 days under 5% carbon dioxide conditions.

(3) Neutral Red Uptake Assay

Cytopathic effect (CPE) observed along with influenza virus proliferation was assessed by the methods described in J. Virol. Methods, 2002, vol. 106, p. 71-79 and Proc. Natl. Acad. Sci., 1998, vol. 95, p. 8874-8849.

After the completion of culture, a 0.033% neutral red solution diluted with a calcium/magnesium-free Dulbecco's phosphate buffer was added at a volume of 100 μl to each well. The plate was allowed to stand at 35° C. under 5% carbon dioxide conditions. Two hours later, the solutions in the wells were removed by aspiration. After rinsing twice with 100 μL of a calcium/magnesium-free Dulbecco's phosphate buffer, 100 μL of a mixed solution of a buffer (pH 4.2; composed of 0.1 mol/L sodium citrate and 0.1 mol/L hydrochloric acid) and ethanol at 1:1 ratio by volume was added to each well. The plate was allowed to stand at room temperature, protected from light. Thirty minutes later, absorbance (540 nm) was measured using a microplate reader (BIO-RAD Model 550). Uninfected controls were prepared by adding, instead of the influenza virus solution, 50 μL of an Eagle's MEM medium containing TPCK-treated trypsin at four times the concentration of the test medium and subjected to the same procedures as those for the test group, followed by absorbance measurement. For blank, wells without being inoculated with the MDCK cells were subjected to the same procedures as those for the uninfected controls, followed by absorbance measurement. Eight wells were used in each concentration. An average value was used, and a numeric value obtained by subtracting the absorbance of blank from the measured value was used for following calculation as absorbance. A value obtained by subtracting the absorbance of infected controls from that of the uninfected controls was used as a value of complete inhibition of virus proliferation. The inhibition rate of virus proliferation in each test was calculated according to the following formula:

Inhibition rate of virus proliferation=[(Absorbance of single drug or combined drugs)−(Absorbance of infected control)]/[(Absorbance of uninfected control)−(Absorbance of infected control)].

(4) Analysis of Combination Effects

From the concentrations of single drugs and two drugs used in combination, the ratio of the combination drugs, and the inhibition rate of virus proliferation, the combination effects were analyzed using SAS release 8.2 (SAS Institute Japan Ltd.) according to the Median effect method of Chou et al. Of methods shown in Advanced Enzyme Regulation, 1984, vol. 22, p. 27-55, an equation for drugs whose mechanisms of action are completely independent from each other (mutually nonexclusive drugs) was used to calculate a CI value. The combination effects were determined based on a CI value at 50% inhibition of virus proliferation according to the description of the paper of Taira et al. [Acta Medica Okayama., 2006, vol. 60, p. 25-34] wherein CI≤0.8 represents synergism, 0.8<CI<1.2 represents additivity, and 1.2≤CI represents antagonism.

The inhibition rates of virus proliferation of T-705 singly used, GS-4071 singly used, and the combination of these drugs are shown in Table 1. Results of analysis using these values are shown in Table 2.

TABLE 1

| Single use of T-705 | | Single use of GS-4071 | | Combined use of T-705 and GS-4071 | |
|---|---|---|---|---|---|
| Conc. (μg/mL) | Inhibition rate | Conc. (μg/mL) | Inhibition rate | Conc. (μg/mL) | Inhibition rate |
| 0.0156 | 0.019 | 0.00313 | 0.019 | 0.01873 | 0.040 |
| 0.0313 | 0.067 | 0.00625 | 0.11 | 0.03755 | 0.21 |
| 0.0625 | 0.097 | 0.0125 | 0.14 | 0.075 | 0.41 |
| 0.125 | 0.27 | 0.025 | 0.25 | 0.15 | 0.59 |
| 0.25 | 0.43 | 0.05 | 0.29 | 0.3 | 0.73 |
| 0.5 | 0.60 | 0.1 | 0.42 | 0.6 | 0.96 |
| 1 | 0.85 | 0.2 | 0.61 | 1.2 | 0.88 |
| 2 | 0.93 | 0.4 | 0.73 | 2.4 | 0.95 |
| 4 | 1.0 | 0.8 | 0.84 | 4.8 | 0.94 |

TABLE 2

| Ratio of combined drugs (T-705:GS-4071) | CI value at 50% inhibition |
|---|---|
| 5:1 | 0.66 |

The combined administration of T-705 and GS-4071 (in-vivo active form of oseltamivir) exhibited more excellent synergistic inhibitory effects on virus proliferation than that exhibited by the single-drug administration.

Test Example 2

T-705 was selected as a test compound. Zanamivir was selected as a neuraminidase inhibitor. A test was conducted in the same way as in the method described in Test Example 1.

The inhibition rates of virus proliferation of T-705 singly used, zanamivir singly used, and the combination of these drugs are shown in Table 3. Results of analysis using these values are shown in Table 4.

TABLE 3

| Single use of T-705 | | Single use of Zanamivir | | Combined use of T-705 and Zanamivir | |
|---|---|---|---|---|---|
| Conc. (μg/mL) | Inhibition rate | Conc. (μg/mL) | Inhibition rate | Conc. (μg/mL) | Inhibition rate |
| 0.0625 | 0.062 | 0.0031 | 0.062 | 0.01875 | 0.10 |
| 0.125 | 0.17 | 0.00625 | 0.12 | 0.0375 | 0.23 |
| 0.25 | 0.34 | 0.0125 | 0.23 | 0.075 | 0.38 |
| 0.5 | 0.64 | 0.025 | 0.28 | 0.15 | 0.69 |
| 1 | 0.77 | 0.05 | 0.49 | 0.3 | 0.87 |
| 2 | 0.89 | 0.1 | 0.60 | 0.6 | 0.94 |
| | | 0.2 | 0.67 | | |
| | | 0.4 | 0.75 | | |

TABLE 4

| Ratio of combined drugs (T-705:Zanamivir) | CI value at 50% inhibition |
|---|---|
| 5:1 | 0.38 |

The combined administration of T-705 and zanamivir exhibited more excellent synergistic inhibitory effects on virus proliferation than that exhibited by the single-drug administration.

Test Example 3

T-705 was selected as a test compound. GS-4071 was selected as a neuraminidase inhibitor. A test was conducted in the same way as in the method described in Test Example 1 using Victoria/3/75 (H3N2) as influenza virus.

The inhibition rates of virus proliferation of T-705 singly used, GS-4071 singly used, and the combination of these drugs are shown in Table 5. Results of analysis using these values are shown in Table 6.

TABLE 5

| Single use of T-705 | | Single use of GS-4071 | | Combined use of T-705 and GS-4071 | |
|---|---|---|---|---|---|
| Conc. (μg/mL) | Inhibition rate | Conc. (μg/mL) | Inhibition rate | Conc. (μg/mL) | Inhibition rate |
| 0.125 | 0.026 | 0.003125 | 0.086 | 0.01875 | 0.15 |
| 0.25 | 0.09 | 0.00625 | 0.14 | 0.0375 | 0.37 |
| 0.5 | 0.42 | 0.0125 | 0.44 | 0.075 | 0.72 |
| 1 | 0.76 | 0.025 | 0.54 | 0.15 | 0.92 |
| 2 | 0.86 | 0.05 | 0.68 | 0.3 | 1.03 |
| 4 | 0.94 | 0.1 | 0.80 | | |
| | | 0.2 | 0.88 | | |

TABLE 6

| Ratio of combined drugs (T-705:GS-4071) | CI value at 50% inhibition |
|---|---|
| 5:1 | 0.36 |

The combined administration of T-705 and GS-4071 (in-vivo active form of oseltamivir) exhibited more excellent synergistic inhibitory effects on virus proliferation than that exhibited by the single-drug administration.

Test Example 4

T-705 was selected as a test compound. Zanamivir was selected as a neuraminidase inhibitor. A test was conducted in the same way as in the method described in Test Example 3.

The inhibition rates of virus proliferation of T-705 singly used, zanamivir singly used, and the combination of these drugs are shown in Table 7. Results of analysis using these values are shown in Table 8.

TABLE 7

| Single use of T-705 | | Single use of Zanamivir | | Combined use of T-705 and Zanamivir | |
|---|---|---|---|---|---|
| Conc. (μg/mL) | Inhibition rate | Conc. (μg/mL) | Inhibition rate | Conc. (μg/mL) | Inhibition rate |
| 0.125 | 0.026 | 0.0125 | 0.074 | 0.01875 | 0.032 |
| 0.25 | 0.092 | 0.025 | 0.14 | 0.0375 | 0.12 |
| 0.5 | 0.42 | 0.05 | 0.27 | 0.075 | 0.27 |
| 1 | 0.76 | 0.1 | 0.40 | 0.15 | 0.70 |
| 2 | 0.86 | 0.2 | 0.60 | 0.3 | 0.87 |
| 4 | 0.94 | 0.4 | 0.71 | 0.6 | 0.94 |
| | | 0.8 | 0.81 | | |

TABLE 8

| Ratio of combined drugs (T-705:Zanamivir) | CI value at 50% inhibition |
|---|---|
| 5:1 | 0.25 |

The combined administration of T-705 and zanamivir exhibited more excellent synergistic inhibitory effects on virus proliferation than that exhibited by the single-drug administration.

As seen from the results, the combined administration of a pyrazine derivative represented by the general formula [1] or a salt thereof and various neuraminidase inhibitors exhibits synergistic anti-influenza virus activities and is effective for the treatment (e.g., therapy or prevention) of influenza.

INDUSTRIAL APPLICABILITY

A pharmaceutical composition comprising a pyrazine derivative or a salt thereof and one or more neuraminidase inhibitor(s) has synergistic strong anti-influenza virus activities and is useful for the treatment (e.g., therapy or prevention) of influenza. A method of using these compounds in combination is useful as a method of treatment (e.g., therapy or prevention) of influenza.

The invention claimed is:

1. A pharmaceutical composition for treating influenza virus infection, comprising (A) a pyrazine derivative represented by the following general formula or a salt thereof; and (B) a neuraminidase inhibitor selected from the group consisting oseltamivir, zanamivir, peramivir, and CS-8958:

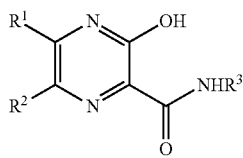

[Formula 1]

wherein $R^1$ is a hydrogen atom, $R^2$ is fluorine, and $R^3$ is a hydrogen atom, and wherein (A) and (B) are in synergistic and effective amounts.

2. The pharmaceutical composition according to claim 1, wherein the neuraminidase inhibitor is oseltamivir or zanamivir.

3. The pharmaceutical composition according to claim 1, wherein the neuraminidase inhibitor is oseltamivir.

4. The pharmaceutical composition according to claim 1, wherein the neuraminidase inhibitor is zanamivir.

5. The pharmaceutical composition according to claim 1, wherein the neuraminidase inhibitor is peramivir.

6. The pharmaceutical composition according to claim 1, wherein the neuraminidase inhibitor is CS-8958.

7. A method of treating an influenza virus infection in a subject in need thereof, the method comprising administering to the subject (A) a pyrazine derivative represented by the following general formula or a salt thereof; and (B) a neuraminidase inhibitor selected from the group consisting of oseltamivir, zanamivir, peramivir, and CS-8958:

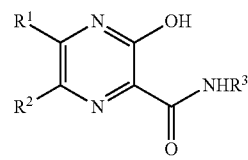

[Formula 2]

wherein $R^1$ is a hydrogen atom, $R^2$ is a fluorine atom, and $R^3$ is a hydrogen atom, and wherein (A) and (B) are in synergistic and effective amounts.

8. The method according to claim 7, wherein the neuraminidase inhibitor is oseltamivir or zanamivir.

9. The method according to claim 7, wherein the neuraminidase inhibitor is oseltamivir.

10. The method according to claim 7, wherein the neuraminidase inhibitor is zanamivir.

11. The method according to claim 7, wherein the neuraminidase inhibitor is peramivir.

12. The method according to claim 7, wherein the neuraminidase inhibitor is CS-8958.

* * * * *